United States Patent
Vaira (10) Patent No.: US 12,029,768 B2
(45) Date of Patent: Jul. 9, 2024

(54) PROBIOTICS USEFUL FOR ERADICATING HELICOBACTER PYLORI INFECTION

(71) Applicant: DACF S.r.l., Bologna (IT)

(72) Inventor: Berardino Vaira, Bologna (IT)

(73) Assignee: DACF S.R.L., Bologna (IT)

( * ) Notice: Subject to any disclaimer, the term of this patent is extended or adjusted under 35 U.S.C. 154(b) by 550 days.

(21) Appl. No.: 17/287,238

(22) PCT Filed: Oct. 23, 2019

(86) PCT No.: PCT/EP2019/078872
§ 371 (c)(1),
(2) Date: Apr. 21, 2021

(87) PCT Pub. No.: WO2020/083983
PCT Pub. Date: Apr. 30, 2020

(65) Prior Publication Data
US 2021/0379125 A1  Dec. 9, 2021

(30) Foreign Application Priority Data
Oct. 24, 2018  (IT) ........................ 102018000009755

(51) Int. Cl.
*A61K 35/745* (2015.01)
*A61K 31/43* (2006.01)
*A61K 31/7048* (2006.01)
*A61K 35/747* (2015.01)
*A61P 31/04* (2006.01)
*C12N 1/20* (2006.01)
*C12R 1/23* (2006.01)

(52) U.S. Cl.
CPC ............ *A61K 35/745* (2013.01); *A61K 31/43* (2013.01); *A61K 31/7048* (2013.01); *A61K 35/747* (2013.01); *A61P 31/04* (2018.01); *C12N 1/205* (2021.05); *C12R 2001/23* (2021.05)

(58) Field of Classification Search
CPC ...... A61K 35/12; A61K 35/74; A61K 35/741; A61K 35/747
See application file for complete search history.

(56) References Cited

FOREIGN PATENT DOCUMENTS

| | | |
|---|---|---|
| CN | 105002125 A | 10/2015 |
| CN | 105087439 A | 11/2015 |
| EP | 1107772 B1 | 4/2006 |

OTHER PUBLICATIONS

What is H. pylori, WebMD, https://www.webmd.com/digestive-disorders/h-pylori-helicobacter-pylori, accessed Sep. 27, 2023 (Year: 2023).*
J.M.T. Hamilton-Miller, "The Role of Probiotics in the Treatment and Prevention of Helicobacter Pylori Infection", International of Antimicrobial Agents, vol. 22, No. 4, pp. 360-366, 2003.
Damien Paineau, et al., "Effects of Seven Potential Probiotic Strains On Specific Immune Responses in Healthy Adults: a Double-Blind, Randomized, Controlled Trail", FEMS Immunology and Medical Microbiology, vol. 53, No. 1, pp. 107-113, 2008.
International Search Report and Written Opinion for Corresponding International Application No. PCT/EP2019/078872 (13 Pages) (Dec. 11, 2019).
International Preliminary Report on Patentability for Corresponding International Application No. PCT/EP2019/078872 (17 Pages) (Mar. 16, 2021).

\* cited by examiner

*Primary Examiner* — Brian Gangle
*Assistant Examiner* — Lakia J Jackson-Tongue
(74) *Attorney, Agent, or Firm* — LUCAS & MERCANTI, LLP (57) ABSTRACT

New probiotic clones have been obtained having enhanced activity against *Helicobacter pylori* infection. The new clones are derived from selected strains of *Lactobacillus acidophilus* and *Bifidobacterium animalis lactis* sp. They are advantageously non-susceptible to antibiotics currently used in the treatment of *Helicobacter pylori* infection, which makes them ideal for co-treatment with said antibiotics in the eradication of *Helicobacter pylori* infection. Synergistic effects of combinations among the present probiotics and their strong adjuvant effect on the activity of antibiotics on *Helicobacter pylori* are herein reported.

13 Claims, 3 Drawing Sheets
Specification includes a Sequence Listing.

Figure 1

|   | 1 | 2 | 3 | 4 | 5 | 6 |
|---|---|---|---|---|---|---|
| A | a 100ul dil 1/128 | b 100ul dil 1/128 | 1/256 b + 1/2 a | 1/256 b + 1/4 a | 1/256 b + 1/8 a | 1/256 b + 1/16 a |
| B | a 100ul dil 1/64 | b 100ul dil 1/64 | 1/128 b + 1/2 a | 1/128 b + 1/4 a | 1/128 b + 1/8 a | 1/128 b + 1/16 a |
| C | a 100ul dil 1/32 | b 100ul dil 1/32 | 1/64 b + 1/2 a | 1/64 b + 1/4 a | 1/64 b + 1/8 a | 1/64 b + 1/16 a |
| D | a 100ul dil 1/16 | b 100ul dil 1/16 | 1/32 b + 1/2 a | 1/32 b + 1/4 a | 1/32 b + 1/8 a | 1/32 b + 1/16 a |
| E | a 100ul dil 1/8 | b 100ul dil 1/8 | 1/16 b + 1/2 a | 1/16 b + 1/4 a | 1/16 b + 1/8 a | 1/16 b + 1/16 a |
| F | a 100ul dil 1/4 | b 100ul dil 1/4 | 1/8 b + 1/2 a | 1/8 b + 1/4 a | 1/8 b + 1/8 a | 1/8 b + 1/16 a |
| G | a 100ul dil 1/2 | b 100ul dil 1/2 | 1/4 b + 1/2 a | 1/4 b + 1/4 a | 1/4 b + 1/8 a | 1/4 b + 1/16 a |
| H | a 100ul | b 100ul | 1/2 b + 1/2 a | 1/2 b + 1/4 a | 1/2 b + 1/8 a | 1/2 b + 1/16 a |
|   | A only | B only | A+B |   |   |   |

| 7 | 8 | 9 | 10 | 11 | 12 |
|---|---|---|---|---|---|
| 1/256 b + 1/32 a | 1/256 b + 1/64 a | 1/256 b + 1/128 a | 1/256 b + 1/256 a | 1/256 b + 1/512 a | NEG CTR |
| 1/128 b + 1/32 a | 1/128 b + 1/64 a | 1/128 b + 1/128 a | 1/128 b + 1/256 a | 1/128 b + 1/512 a | 1/128 b + 1/1024 a |
| 1/64 b + 1/32 a | 1/64 b + 1/64 a | 1/64 b + 1/128 a | 1/64 b + 1/256 a | 1/64 b + 1/512 a | 1/64 b + 1/1024 a |
| 1/32 b + 1/32 a | 1/32 b + 1/64 a | 1/32 b + 1/128 a | 1/32 b + 1/256 a | 1/32 b + 1/512 a | 1/32 b + 1/1024 a |
| 1/16 b + 1/32 a | 1/16 b + 1/64 a | 1/16 b + 1/128 a | 1/16 b + 1/256 a | 1/16 b + 1/512 a | 1/16 b + 1/1024 a |
| 1/8 b + 1/32 a | 1/8 b + 1/64 a | 1/8 b + 1/128 a | 1/8 b + 1/256 a | 1/8 b + 1/512 a | 1/8 b + 1/1024 a |
| 1/4 b + 1/32 a | 1/4 b + 1/64 a | 1/4 b + 1/128 a | 1/4 b + 1/256 a | 1/4 b + 1/512 a | 1/4 b + 1/1024 a |
| 1/2 b + 1/32 a | 1/2 b + 1/64 a | 1/2 b + 1/128 a | 1/2 b + 1/256 a | 1/2 b + 1/512 a | 1/2 b + 1/1024 a |

PROBIOTICS USEFUL FOR ERADICATING HELICOBACTER PYLORI INFECTION

CROSS-REFERENCE TO RELATED APPLICATIONS

This application is a 371 of PCT/EP2019/078872, filed Oct. 23, 2019, which claims the benefit of Italian Patent Application No. 102018000009755, filed Oct. 24, 2018.

FIELD OF THE INVENTION

The present invention relates to the field of probiotic microorganisms and their use in medicine, in particular, in the treatment and prevention of bacterial infections. The invention further concerns the modification of probiotic microorganisms for the purpose of improving their therapeutic effectiveness, in particular in the area of treatment and prevention of *Helicobacter pylori* infection.

STATE OF THE ART

*Helicobacter pylori* is a gram negative, acid-tolerant and capnophilic microorganism that found its niche in the human stomach and evolved together with man. At present, this species infects more than 50% of the adult global population (Hooi). Colonization of the gastric mucosa stimulates an intense local and systemic inflammatory and immune response, which, in concert with toxic substances produced by the bacteria, causes peptic ulceration in 10%-20% and gastric cancer in 1%-3% of infected individuals (Suerbaum S, Michetti P).

Eradication of infection can be attained by treatment with a proton pump inhibitor (PPI) associated with antibiotics like amoxicillin, clarithromycin, a nitroimidazole, a fluoroquinolone and tetracycline, often used in combination (Malfertheiner). The long-lasting use of these antibiotics ended to select chemoresistant strains, with a consequent consistent reduction of the healing rates. In addition, the antibiotic administration often determines adverse effects that in many cases may lead to the suspension of treatment (Alba).

The administration of probiotic microorganisms (probiotics) in addition to the classic protocols of cure has recently ensured some improvement of therapeutic success in terms of increment of eradication percentages and reduction of undesirable effects (Dang). Probiotics used more frequently belong to the genera *Lactobacillus* and *Bifidobacterium*. *Lactobacillus acidophilus* and *Bifidobacterium lactis* are the species employed more often as their administration to human beings has been considered safe (Dang, Borriello). These organisms are acid- and bile-tolerant; they adhere to cells in vitro and may exert a bactericidal activity against *H. pylori* by producing acids, bacteriocines etc. cfr. e.g. US2016/0279180.

The publication International Journal of Antimicrobial Agents, 22, 2003 p. 360-366 describes an in-vitro inhibitory activity on *H. pylori* for specific strains of *Lactobacillus acidophilus* (strains CRL639, LB, NAS, DDS-1) and of *Bifidobacterium longum* (BB536); the activity is described as strain-dependent; the document also reviews a number of studies using probiotic microorganisms in co-therapy with antibiotics showing inconsistent effects on *H. pylori* eradication: in particular *Lactobacillus* probiotics from different sources were found either effective or ineffective. In a pilot study published in FEMS Immunology and Medical Microbiology, 53(1), 2008, p. 107-113, a partial immunoglobuline-enhancing effect has been reported for some strains of *Bifidobacterium lactis* (Bi-07, Bl-04), *Lactobacillus acidophilus* (La-14, NCFM), *Lactobacillus plantarum* (Lp-115), *Lactobacillus paracasei* (Lpc-37), *Lactobacillus salivaris* (Ls-33); the effect was limited to IgG, not on IgA or IgM; these probiotics were described as potentially useful to increase the effects of oral vaccination (the study was limited to patients under cholera vaccination), however the overall vaccination title was not increased. The patent application EP 2 270 133 discloses two strains of *Bifidobacterium bifidus* (respectively CP5 and LGG) having antibacterial against *H. pylori*, and being resistant to various antibiotic agents; the document attributes the antibacterial activity on *H. pylori* to specific peptide metabolites produced by these particular probiotic, which are not produced by other strains of the same species. Overall, the above results highlight a large variability of antibacterial effects, even among different strains of the same probiotic species, causing them to be unpredictably effective or ineffective on the eradication of infection; it also shows the complex reaction on the immune system caused by some probiotic strains in presence of the cholera toxin and the difficulty to derive therefrom a concretely effective immune stimulating utility, especially when in presence of different toxins.

Strains of *Bifidobacterium animalis lactis* (LAFTI® B94, Lallemand Health Solutions) are also used for treating diseases other than *H. pylori* infection, e.g. irritable bowel syndrome. Probiotics may also improve the immune response to gut pathogens. The immunomodulation can be attained by inhibiting immunocytes to produce pro-inflammatory and/or stimulating them to secrete anti-inflammatory cytokines (Foligne). However, results obtained in this area have been inconsistent, with improved eradication of *H. pylori* in some studies and no significant effects in others (Cekin). In particular, large variations of activity on *H. pylori* have been reported among *Lactobacillus acidophilus* and *Bifidobacterium animalis lactis* of different origins, thus preventing a generalizability of activity among these strains (Dang). The susceptibility of probiotics to the antibiotics commonly used in the treatment of *H. pylori* is also a factor limiting the real-life effectiveness of the probiotic/antibiotic combined therapy; in particular, *Lactobacillus* spp., including *L. acidophilus*, are generally susceptible to amoxicillin—which is the key of all therapeutic protocols for *H. pylori* eradication—and clarithromycin (Štšepetova). *B. lactis* is also susceptible to amoxicillin (Morovic). Susceptibility to erythromycin (representing macrolides) is intermediate, i.e., low; but the levels of macrolides in the stomach (after administration of a dose therapeutically effective) are in all likelihood far higher than their minimal inhibitory concentrations (MIC) against *H. pylori*. Strains of *Bifidobacterium* were found variably susceptible to clarithromycin, which may account for their limited success as adjuvant for this antibiotic in treating *H. pylori* infection. (Collado). Combinations of probiotics including *Lactobacillus* and *Bifidobacterium* species were used as adjuvant to the antibiotic treatment of *H. pylori* infection, however also in this case with inconsistent results (review in McFarland).

Therefore, the need remains to make available effective treatments of *H. pylori* infection involving the use of probiotic agents. A particular need is to find consistently effective probiotics, i.e. showing stable and reproducible levels of activity, in particular when used in combination with specific antibiotic therapies. A further need is to strongly improve the effectiveness of known antibiotic mixtures in the treatment of *H. pylori*, e.g. via strong enhancements and/or synergisms in the overall *H. pylori* eradication rate. A further need is to identify agents reliably capable to obtain a reduction in the side effects of antibiotic used in treatment protocols for *H. pylori* infection, without prejudice to the antibiotic level of activity.

SUMMARY

New probiotic clones have now been obtained showing a particularly high activity against *Helicobacter pylori* infection. The new clones have been derived from *Lactobacillus acidophilus*, strain La-14 and *Bifidobacterium animalis lactis*, strain Bl-04, both being naturally resistant to levofloxacin and metronidazole. The present new clones have antibacterial, growth-inhibiting activity on *Helicobacter pylori* and are resistant to the antibiotics amoxicillin and/or clarithromycin, which are typically used in the treatment of *Helicobacter pylori* infection: this makes them ideal for the treatment of *Helicobacter pylori* infection, alone or in combination with said antibiotics. The stability of the levels of resistance of the new clones to specific antibiotics has been verified.

Synergistic effects of mutual combinations of the new probiotics, as well as their dramatic contribution to *H. pylori* inhibiting effects of antibiotics like clarithromycin or amoxicillin are further herein disclosed.

DESCRIPTION OF THE FIGURES

FIG. 2: checkerboard dilutions scheme: In column 1: scalar dilutions of antibiotics (amoxicillin or clarithromycin). In column 2: scalar dilutions of mixed supernatants (*L. acidophilus* or *B. lactis* from overnight culture in broth). From column 3 to 12: different combinations of supernatant and antibiotic concentrations. A12 well: positive control

DETAILED DESCRIPTION OF THE INVENTION

The term "clone" used herein means a fraction of microorganisms derived by selection from a broader original population of microorganisms; compared to the original population, the microorganisms of the clone will show more homogeneous features; the term "clone" also encompasses possible "sub-clones" obtained by further selection(s) from a precedent clone; the term "selection" used herein does not exclude the possibility of structural or genetic modification of microorganisms occurring during the selection process, such that the final clone population may include microorganism not originally present within the original population. The terms "clone" or "clones" is herein indifferently referred to any of the new clones of the invention, unless differently specified; the clones of the invention may also be referred herein as "the present clones", "the clones of the present invention", "the probiotics of the invention", "the probiotic microorganisms of the invention", "the present probiotics", "the probiotic microorganisms of the present invention", all of which are used herein as synonymous.

Whenever used herein, the term "association" means the co-presence and/or joint use of the associated items.

The terms "co-treatment" or "combined treatment" are herein synonymous and refer to a treatment using two or more active agents, as specified in the context.

The term "co-formulation" or "co-formulated" means the formulation of two or more ingredients within the same product.

When used in reference to the present clones, the term "antibiotic resistance" means the resistance of the clone to the growth-inhibiting activity of the antibiotic; this property is also indicated as "non-susceptibility" or "chemoresistance", all being used herein as synonyms.

A first object of the present invention are new clones of specific probiotic microorganism strains, said clones being selected and isolated for the first time by the present Applicant. The probiotic microorganism strains, source of the present clones are *Lactobacillus acidophilus*, strain La-14 and *Bifidobacterium animalis lactis*, strain Bl-04. The new clones, object of the invention, are the following:

*Lactobacillus acidophilus* La-14, clone LAA8, with deposit number: DPS RE RSCIC 5;

*Lactobacillus acidophilus* La-14, clone LACE, with deposit number: DPS RE RSCIC 6;

*Bifidobacterium animalis lactis* Bl-04, clone BLAC86, with deposit number: DPS RE RSCIC 7;

*Bifidobacterium animalis lactis* Bl-04, clone BLAB, with deposit number: DPS RE RSCIC 8; and

*Bifidobacterium animalis lactis* Bl-04, clone BLC6, with deposit number: DPS RE RSCIC 9.

The five clones of the present invention have been filed on Aug. 31, 2018 under the Budapest Treaty at the Istituto Zooprofilattico Sperimentale della Lombardia e dell'Emilia Romagna at Via A. Bianchi, 9-25128 Brescia, Italy, and are primarily characterized by their deposit numbers. They are further characterized by their taxonomic origin, being specifically derived from the strains: *Lactobacillus acidophilus* La-14 or *Bifidobacterium animalis lactis* 31-04. These strains are commercially available and can be obtained e.g. from Florafit® Probiotics, Dupont Nabisco (*B. animalis lactis* Bl-04 (ATCC: SD5219) and *L. acidophilus* La-14 (ATCC: SD5212) or from Prolife® Vis, Zeta Farmaceutici) The terms LAA8, LACE, BLAC86, BLA8 and BLC6 are new and used herein by the Applicant to indicate each of the different clones of the invention. The above deposited clones may also be characterized by their genetic sequencing, as detailed in the experimental section.

The clones of the present invention are further characterized by their pharmacological activities. They have in fact a number of interesting properties, namely: (a) a remarkable activity against *Helicobacter pylori*; (b) an unexpected synergistic activity on *Helicobacter pylori* when used in mutual combinations; (c) a remarkably high resistance (i.e. non-susceptibility) to antibiotics (in particular clarithromycin and/or amoxicillin), commonly used for the eradication of *Helicobacter pylori* which makes them best useful in a combined treatment of *Helicobacter pylori* infection in association with said antibiotics; (d) an unexpectedly high adjuvant effect in inhibiting the growth of *Helicobacter pylori* infection, when used in association with said antibiotics.

The activity of the present clones in inhibiting the growth of *H. pylori* can be assessed by conventional methods, e.g. by seeding the concerned clone on a solid culture of *H. pylori* and verifying the formation/30 extension of a growth-inhibition zone in correspondence of the seeding site; as an alternative example, the clones activity can be assessed by the "agar well diffusion method", wherein probiotic suspensions are inserted into wells dug in agar plates, on which *H. pylori* is cultured. After incubation, Inhibition zones are detectable.

The synergy among two or more of the present clones in inhibiting the growth of *H. pylori* can be assessed by eliciting more than additive effects of the combined vs. separate clones; the assessment can be made via conventional methods, e.g. by separately seeding the concerned clones in partially overlapping areas of a solid culture of *H. pylori* (cf. e.g. cross-shaped seeding) and comparing the formation/extension of a growth inhibition zone in correspondence of the seeding sites, both in the overlapping and non-overlapping areas. All the combinations of the present new clones are part by the present invention; preferred combinations are those comprising:

(i) one or more among *Lactobacillus acidophilus* La-14 clone LAA8 (deposit number: DPS RE RSCIC 5) and *Lactobacillus acidophilus* La-14 clone LAC6 (deposit number: DPS RE RSCIC 6), and (ii) one or more among *Bifidobacterium animalis lactis* Bl-04 clone BLAC86 (deposit number: DPS RE RSCIC 7); *Bifidobacterium animalis lactis* Bl-04 clone BLA8 (deposit number: DPS RE RSCIC 8); and *Bifidobacterium animalis lactis* Bl-04 clone BLC6 (deposit number: DPS RE RSCIC 9).

The level of resistance (non-susceptibility) of the present clones to a given antibiotic can be assessed as the minimum inhibitory concentration (MIC) of the antibiotic on the growth of the concerned clone: a high MIC denotes a high resistance of the concerned clone. The resistance to antibiotics shown by the present clones is particularly advantageous because it concerns antibiotics currently used for the eradication of *H. pylori* infection, in particular amoxicillin, clarithromycin and their analogues; the achievement of this result is even more remarkable, considering that *Lactobacillus* and *Bifidobacterium* sp. are normally sensible to such antibiotics. Contrary to the praxis in other medical treatments, the antibiotic resistance typical of the present probiotic clones is desirable because it permits using them in co-treatment with the antibiotic without being inhibited by the same; even after eradication of *H. pylori* infection, the acquired antibiotic resistance of the present probiotic remains beneficial for the patient because the species in question (*Lactobacillus*, *Bifidobacterium*) are natural components of the intestinal flora and are easily integrated therein in resistant form, thus protecting patient's intestinal function also in case of future antibiotic treatments. As supported in the experimental section, all the present clones are characterized by a high resistance towards amoxicillin and/or clarithromycin and their analogues; the clones of the invention showed a level of antibiotic resistance (expressed as MIC of the corresponding antibiotic on the growth of the relevant clone) higher than 5 μM/mL, which is generally regarded as a high level of antibiotic resistance. Specifically, the clones LAA8 and BLA8 were found highly resistant to amoxicillin; the clones LACE and BLC6 were found highly resistant to clarithromycin; the clone BLAC86 was found highly resistant to both amoxicillin and clarithromycin. Due to its broader spectrum of antibiotic resistance, the clone BLAC86 is particularly preferred within the present invention.

The adjuvant effect of the present clones on the activity of antibiotics in the inhibition of *H. pylori* growth can be assessed by standard means, typically by comparing the MIC of the antibiotic on *H. pylori* in absence vs. presence of the concerned clone, where a decrease of the MIC corresponds to an increase in bactericidal activity; in particular, the adjuvant effect of the present clones can be elicited in in-vitro conditions on cultures of *H. pylori*: this is particularly important because it supports a strong "direct" inhibitory effect of the present probiotics on the growth *H. pylori*, i.e. not merely mediated by an indirect immunostimulating effect on the host. As supported in the experimental section, the present clones caused a dramatic increase of bactericide activity of the tested antibiotics, i.e. a 100 to 1000-fold decrease of the corresponding MIC. This effect is further important because it allows, within a probiotic-antibiotic combined treatment, to substantially reduce the amount of administered antibiotic without incurring a reduction of efficacy in the *H. pylori* eradication rate; the lesser amount of administered antibiotic has evident advantages in terms of reduced risk of antibiotic accumulation/side effects for the patient and reduced risk of formation of antibiotic-resistant strains of *H. pylori* to the benefit of the patient and the environment.

A further object of the present invention is the provision of the probiotic microorganisms of the present invention, never isolated and/or characterized before, for use in medicine. A further object of the present invention is the provision of the probiotic microorganisms of the present invention for use in treating or preventing any condition requiring the administration of a probiotic microorganism, wherein the use of the present clones entails special advantages in terms of stability and high level of resistance to future or concomitant antibiotic treatments. The invention further contemplates a method of treating or preventing a condition requiring the administration of a probiotic microorganism, comprising the administration of the probiotic microorganisms here above described to a human or animal patient in need thereof. Examples of conditions requiring probiotic treatment are: alterations in the intestinal flora and associated gastrointestinal disorders, weakened conditions subsequent to diseases affecting the gastrointestinal system, disorders involving a reduction or unbalance in food assimilation, hypersensitivity or intolerance to food ingredients, etc.

A further object of the invention is the provision of the present probiotic microorganisms for use in treating or preventing *Helicobacter pylori* infections. The invention likewise contemplates a method of treating or preventing *Helicobacter pylori* infections, comprising the administration of the probiotic microorganisms here above described to a patient in need thereof. The invention likewise includes the use of the present probiotic microorganisms for the manufacture of a medicament for treating or preventing *Helicobacter pylori* infections.

As reported herein, the new probiotic clones of the present invention are effective in inhibiting the growth of *H. pylori* when used as such, or when used in combination with one another, or when used in combinations with an antibiotic treatment of *H. pylori*, infection.

No specific limitations are foreseen regarding dosages and regimens of administration of the present probiotic microorganisms; these can be readily adapted in function of the specific need of the patient (extent/course of the disease, patient general conditions, etc.). As non-limitative example, daily dosages of the present probiotic microorganisms will be comprised from $10^{\wedge 9}$ to $5 \times 10^{\wedge 11}$ colony-forming units (CFU)/day, preferably from $5 \times 10^{\wedge 9}$ to $2.5 \times 10^{\wedge 11}$ CFU/day, more preferably from $8 \times 10^{\wedge 9}$ to $1.5 \times 10^{\wedge 11}$ CFU/day, for example about $10^{\wedge 10}$ can be mentioned; when one or more probiotic microorganisms are used in combination, the above dosage intervals are meant to be referred to the whole of microorganisms used.

When used in a co-treatment of *H. pylori* infection with antibiotic agents, the present methods incur the special advantage of relying on probiotic microorganisms being directly effective on *H. pylori* and being highly resistant to the antibiotics commonly used against this pathogen, typically clarithromycin, amoxicillin and their analogues. No specific limitation is foreseen regarding formulation, dosages and regimens: for example, the antibiotic can be co-formulated with the probiotic in the same dosage form, or be formulated separately via an independent dosage form: in the latter case the treatment can be performed by assuming the separate dosage forms in any order and at any time distance from one another, provided that at least partly overlapping plasmatic concentrations of the two agents can be obtained. Also in case of combined therapy, no specific limitations are foreseen regarding possible dosages/regimens: they can be widely varied depending on the disease course/severity and patient conditions. Non-limitative exemplifications of daily dosages are those presented above.

A further object of the invention is represented by compositions and relevant dosage forms, characterized by containing the present probiotic microorganisms and being suitable for administration to a human or animal patient. For the preparation of the compositions and dosage forms, the present probiotic microorganism can be generally provided in liquid or solid form, for example suspended in an aqueous medium or adsorbed on a suitable support, e.g. a granulate, etc. The final compositions may be in the form of pharmaceutical composition, food integrator or integrated foodstuff, each containing the corresponding pharmaceutically/alimentary acceptable excipients and/or ingredients, well-known in the art. When in form of pharmaceutical compositions or food integrators, the compositions may be administered without limitation via any route of administration; however, considering the intestinal site of action of the current probiotics, the preferred administration route is the oral one. In the latter case, all known dosage form suitable for oral administration are contemplated by the present invention; exemplary dosage forms are, without limitation: tablets, capsules, microcapsules, pills, lozenges, dragees, powders, granulates, microgranulates, pellets, bioadhesive films, solutions, suspensions, emulsions, microemulsions, gels, syrups, elixirs, chewing gum, drops, sprays, aerosols, and the like. When in form of integrated foodstuff, the compositions will be administered by the oral route in any possible form, in presence of customary alimentary ingredients, depending on the chosen foodstuff; examples of possible foodstuff are beverages, fruit juices, yogurts, cremes, spreads, cheeses, snacks, bars, and the like.

For performing the combined probiotic-antibiotic treatments, all the above referred composition may comprise, in addition to the probiotic microorganisms of the invention and the cited excipients/ingredients/foodstuff, one or more antibiotics directed to the treatment of H. pylori infection; said antibiotics are preferably chosen from clarithromycin, amoxicillin and their analogues, the latter being referred herein as "clarithromycin antibiotics" (i.e. antibiotics with macrolide structure) or "amoxicillin antibiotics" (i.e. antibiotics with penicillin structure).

For the combined probiotic-antibiotic treatments, the present composition can also be provided to the user in the form of kit of parts, where the kit comprises a supply of the present probiotic microorganisms and a separate supply of an antibiotic directed against Helicobacter pylori. The above supplies can be provided either for separate or joint administration. For separate administration, the kit could be e.g. in form of blisters containing one or more dosage units containing the probiotic of the invention, and one or more dosage units containing the antibiotic, were the different dosage forms are made identifiable to the user; the kit may include one or more blisters among which the different dosage forms can be variously distributed. For joint administration, the kit may e.g. include means allowing the user to extemporaneously admix the probiotic and the antibiotic into a same carrier prior to administration, thus enabling a simplified simultaneous administration of both agents.

The present invention is now further disclosed in non-limitative manner by the following examples.

EXPERIMENTALS

1. Isolation of New Clones Resistant to Amoxicillin and Clarithromycin

Wild-type *L. acidophilus* La-14 and *B. animalis lactis* Bl-04 (Florafit® Probiotics, Dupont Danisco) were used as starting materials.

The resistance to Amoxicillin (MIC) was relatively low, i.e. 0.5 µg/ml and 0.25 µg/ml for *L. acidophilus* and *B. lactis*, respectively. The resistance to Clarithromycin MIC was also low, i.e. 0.125 µg/ml and 0.016 µg/ml for *L. acidophilus* and *B. lactis*, respectively. The resistant status was stable after repeated freezing/thawing and after lyophilization.

The bacteriostatic activity against *H. pylori* was detected by the Agar Well Diffusion method; bactericidal activity by the Time-kill Curve method.

We isolated five antibiotic-resistant clones after sub-culturing the two wild-type organisms in MRS (De Man Rogosa Sharpe) agar with increasing antibiotic concentrations, starting from ¼ of the original MIC up to 8 µg/ml for amoxicillin and 6 µg/ml for clarithromycin. Strains with the highest possible levels of resistance were sub-cultured several times, frozen in glycerol-broth or lyophilized. After the freezing/lyophilization, chemosusceptibility tests were carried out to confirm the stability of the resistance levels. For both *L. acidophilus* La-14 and *B. animalis lactis* Bl-04, we were able to identify and isolate clones with high resistance to either clarithromicin or amoxicilline; in addition, for *B. animalis lactis* Bl-04 we could identify and isolate a clone with high resistance to both antibiotics. The five isolated clones are listed here below, with indication of their antibiotic resistance (CLA=clarythromicin; AMO=amoxicillin) and deposit number in accordance with the Budapest Treaty:

Lactobacillus acidophilus La-14 clone LAA8 (AMO-resistant)—deposit number: DPS RE RSCIC 5

Lactobacillus acidophilus La-14 clone LAC6 (CLA-resistant)—deposit number: DPS RE RSCIC 6

Bifidobacterium animalis lactis Bl-04 clone BLAC86 (AMO+CLA-resistant)—deposit number: DPS RE RSCIC 7

Bifidobacterium animalis lactis Bl-04 clone BLAB (AMO-resistant)—deposit number: DPS RE RSCIC 8;

Bifidobacterium animalis lactis Bl-04 clone BLC6 (CLA-resistant)—deposit number: DPS RE RSCIC 9.

2. DNA Sequencing

The original wild-type strains and the five isolated clones described above were subjected to DNA sequencing. The DNA of the original strains and of the new chemo resistant probiotics was sequenced by Dr.

Greta Immobile Muraro, Polo d'Innovazione di Genomica, Genetica e Biologia Società Consortile R. L., Siena, by the "Microbial Whole Genome Sequencing 2×150 PE on Illumina MiSeq instrument using MiSeq Reagent Micro Kit (including libraries preparation, clean-up and quantification by Bioanalyzer Coverage up to 100 X. Sequences were also compared with those of the wild strains that are deposited in the genomic bank BLAST/NCBI to testify the complete absence of foreign DNA in the mutant chemo resistant strains.

Compared to the DNA sequence of the wild *L. acidophilus* La-14, amoxicillin-resistant *L. acidophilus* clones harboured 11 mutated sites that can lead up to 112 possible phenotypic variants. Clarithromycin-resistant *L. acidophilus* clones harboured 18 mutated sites, that can lead up to 205 phenotypic variants.

Compared to the DNA sequence of the wild *B. lactis* Bl-04, the amoxicillin and clarithromycin resistant *B. lactis* clone harboured 19 mutated sites, that can lead up to 199 possible phenotypic variants. Clarithromycin resistant *B. lactis* clone harboured 19 mutated sites that can lead up to 199 phenotypic variants. Amoxicillin resistant *B. lactis* clone harboured 11 mutated sites that can lead up to 109 phenotypic variants.

No plasmids have been detected in the original and the antibiotic-resistant strains.

The above referred mutations are described in detail in the following tables:

| Position fragment | Wild-type | Mutated fragment | SEQ.ID.NO: |
|---|---|---|---|
| LAC6 | | | |
| 11784 | G | GGATTC | |
| 81251 | CTTAATTGCTTCT | C | |
| 125357 | GA | G | |
| 278699 | C | T | |
| 291919 | CTGGTCG | C | |
| 294020 | G | GTCACGTAGTTGT | 1 |
| 614078 | A | G | |
| 653065 | C | T | |
| 662525 | GA | G | |
| 734691 | C | T | |
| 941922 | T | C | |
| 1285160 | CA | C | |
| 1304007 | G | A | |
| 1497750 | G | A | |
| 1497825 | C | T | |
| 1497891 | T | G | |
| 1535489 | G | A | |
| 1930513 | G | A | |
| LAA8 | | | |
| 11784 | G | GGATTC | |
| 125375 | GA | G | |
| 165378 | T | TA | |
| 620560 | C | A | |
| 653065 | C | T | |
| 734691 | C | T | |
| 794786 | T | C | |
| 1285160 | CA | C | |
| 1497171 | C | A | |
| 1497750 | G | A | |
| 1497825 | C | T | |
| BLAC86 | | | |
| 37802 | A | G | |
| 97928 | A | T | |
| 101045 | A | G | |
| 135760 | A | G | |
| 165971 | T | C | |
| 214372 | T | C | |
| 265409 | T | C | |
| 610225 | C | A | |
| 625160 | C | A | |
| 708153 | G | T | |
| 925716 | T | C | |
| 1216534 | T | C | |
| 1388583 | C | T | |
| 1388678 | C | T | |
| 1470174 | A | G | |
| 1471473 | CG | C | |
| 1490246 | C | A | |
| 1692246 | T | C | |
| 1853917 | T | C | |

| Position fragment | Wild-type | Mutated fragment | SEQ.ID.NO: |
|---|---|---|---|
| BLA8 | | | |
| 37802 | A | G | |
| 97298 | A | T | |
| 101045 | A | G | |
| 135760 | A | G | |
| 165971 | T | C | |
| 1216534 | T | C | |
| 1388583 | C | T | |
| 1388678 | C | T | |
| 1470174 | A | G | |
| 1692246 | T | C | |
| 1853917 | T | C | |
| BLC6 | | | |
| 37802 | A | G | |
| 97298 | A | T | |
| 101045 | A | G | |
| 135760 | A | G | |
| 165971 | T | C | |
| 214372 | T | C | |
| 265409 | T | C | |
| 610225 | C | A | |
| 625160 | C | A | |
| 708153 | G | T | |
| 925716 | T | C | |
| 1216534 | T | C | |
| 1388583 | C | T | |
| 1388678 | C | T | |
| 1470174 | A | G | |
| 1471473 | CG | C | |
| 1490246 | C | A | |
| 1692246 | T | C | |
| 1853917 | T | C | |

3. Antibiotic Susceptibility Tests

Figure 1:
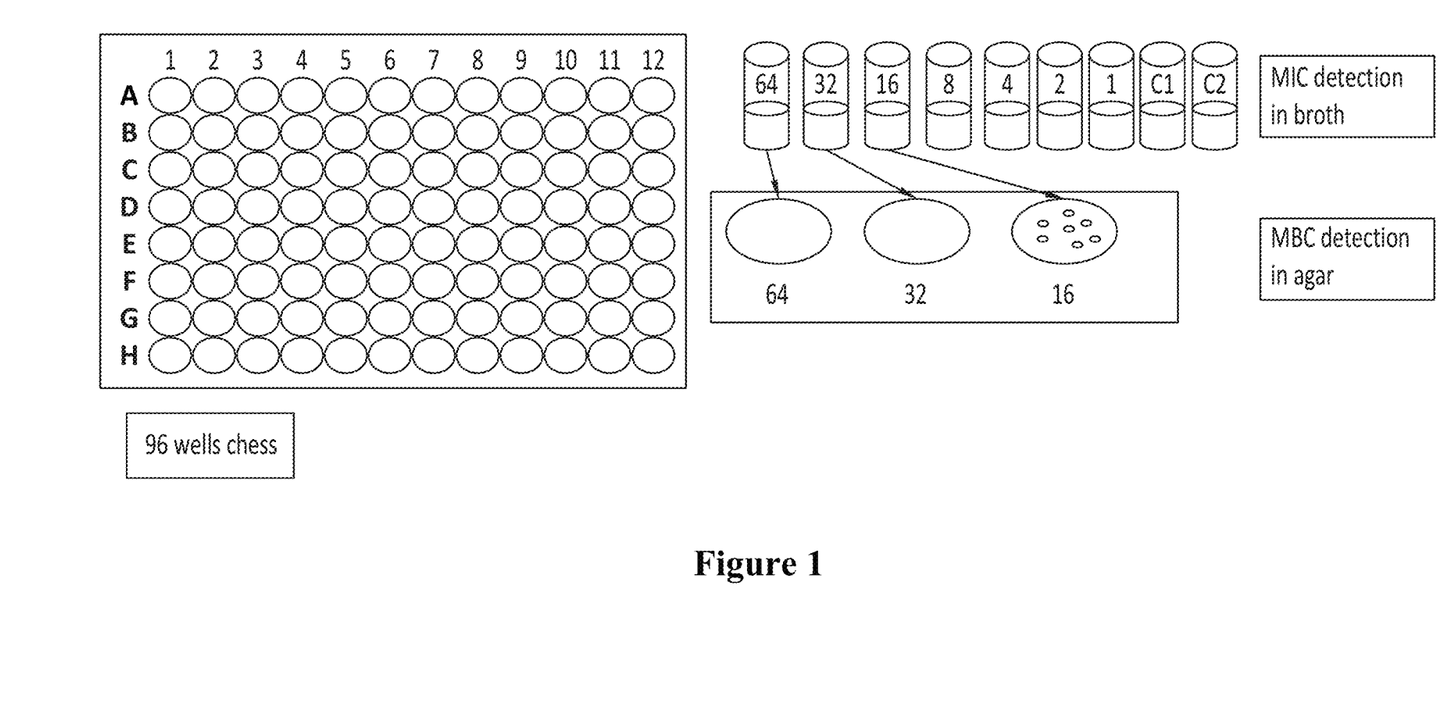
FIG. 1: Broth-Dilution method (Gold Standard method) using 96-well chess-boxes.

The antibiotic susceptibility tests of *H. pylori* and of the probiotic strains were carried out with the Broth-Dilution method (Gold Standard method) using 96-well chess-boxes (FIG. 1). The obtained results indicated an amoxicillin resistance (MIC) of 8 μg/mL for both clones LAA8 and BLAB, a clarithromycin resistance (MIC) resistance of 6 μg/mL for both clones LACE and BLC6, and a dual amoxicillin/clarithromycin resistances (MICs) respectively of 8 and 6 μg/mL for the clone BLAC86; all these values indicate high levels of antibiotic resistance.

4. Evaluation of Synergism

In order to investigate on a possible synergy of growth inhibition between the *Lactobacillus acidophilus* and *Bifidobacterium lactis* strains selected in the frame of the present invention, we performed a cross-shaped seed.

*H. pylori* strains were cultured for 72 hours in selective agar at 37° C. in micro-aerobic conditions, then suspended in sterile saline solution at a density corresponding to 3 McFarland opacity standard and streaked in 3 directions with a swab onto MHF (Mueller Hinton Fastidious) agar plate. In each agar plate *L. acidophilus* La-14 and *B. animalis lactis* Bl-04 were seeded along two perpendicular lines; in each line 10⁻¹⁰ cells ca. were seeded. Then, plates were incubated at 37° C. for 48-72 hours. Afterwards, plates were inspected for the presence of aloes of growth inhibition (see FIG. 3).

La-14 strain and clones were co-seeded with Bl-04 strain and clones to determine the presence of synergism. In negative controls the same strain/clone was used in both perpendicular seeding lines (La-La or Bl-B l). Inhibition zones were measured with a millimeter ruler at the edge of the plate and at ½ of the plate radius (2 cm in our plates).

Figure 3:
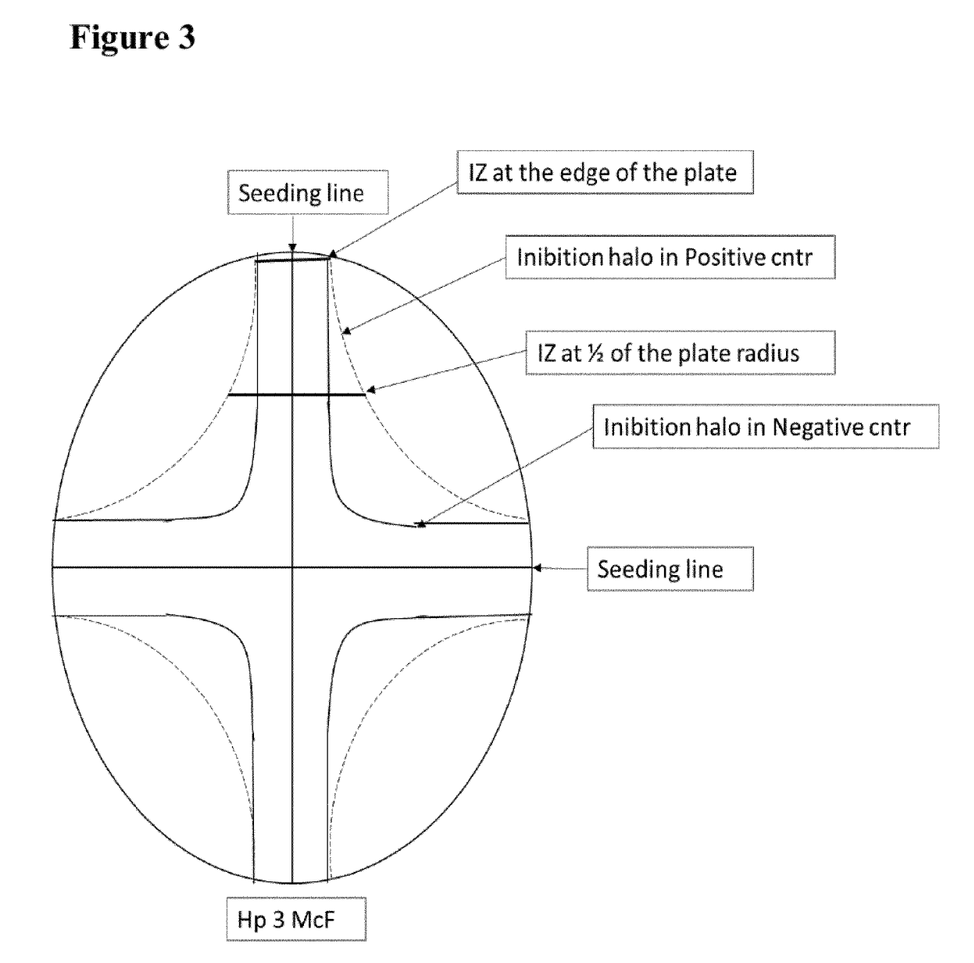
FIG. 3: cross-shaped seeds for bacteriostatic synergy

Inhibition zones at the edge of the plate derive from the single strain's bacteriostatic activity, those near the middle of the plate derive from the activity of both strains (FIG. 3). If inhibition zones tend to increase toward the middle of the plate (dashed line), the bacteriostatic effect is synergistic. In particular, we determined that ½ radius of the plate is a reasonable distance from the intersections of the seedings, so that the inhibition measured here doesn't derive from a mere addition of the respective inhibition zones, highlighting a real synergism. We indeed observed an increase of the inhibition zones from the edge toward the center of the plate, becoming fully evident in the observation zone (middle of the plate radius, at 2 cm from the center) when La strain or clones were co-seeded with Bl strain or clones. This doesn't happen in negative controls (same strain/clone seeded in two perpendicular lines) . . . This synergism was consistently observed in independent experiments performed in different culture media (Muller Hilton Fastidious or *Agar Pylori*), either in absence or presence of antibiotic (amoxicillin and/or clarithromycin, only for clones);. The obtained data are reported in the following table:

| wild pellet in milk | | N. of readings | IZ means mm* edge | half radius** |
|---|---|---|---|---|
| MUELLER HINTON FASTIDIOUS | | | | |
| LA/BL | LA | 2 | 11 | 15 |
| | BL | 2 | 10 | 14.5 |
| LA/LA | | 4 | 12.5 | 12.5 |
| BL/BL | | 4 | 9.5 | 9.5 |
| AGAR PYLORI | | | | |
| LA/BL | LA | 2 | 10 | 16.5 |
| | BL | 2 | 8.5 | 16 |
| LA/LA | | 8 | 6.5 | 6.6 |
| BL/BL | | | 5.5 | 5.7 |
| BLAC86 E LAA8 pellet in milk | | | | |
| MUELLER HINTON FASTIDIOUS | | | | |
| LAA8/BLAC86 | LA | 2 | 10 | 16 |
| | BL | 2 | 10 | 15 |
| LAA8/LAA8 | | 4 | 12.3 | 12.5 |
| BLAC86/BLAC86 | | 4 | 9 | 9 |
| AGAR PYLORI | | | | |
| LAA8/BLAC86 | LA | 2 | 7.5 | 14 |
| | BL | 2 | 6.5 | 11.5 |
| LAA8/LAA8 | | 8 | 7 | 7 |
| BLAC86/BLAC86 | | 4 | 7.5 | 7.5 |
| MHF + antibiotics (0.5 UG/ML AMOXI, 2 UG/ML CLA) | | | | |
| LAA8/BLAC86 | LAA8 | 2 | 10 | 15 |
| | BLAC86 | 2 | 9 | 13 |
| LAA8/LAA8 | | 4 | 10 | 10 |
| BLAC86/BLAC86 | | 4 | 9 | 9 |

*The thickness of the seeding has been substracted
**2 cm

The above reported tests confirm the synergy between the present strains (or the respective clones) in inhibiting the growth of *H. pylori*, since their combined seeding increases the inhibition zone from the edge to the reading point (½ of radius), whereas the inhibition zone derived from the negative control (strain or clone against itself) remains stable at the same reading point. These data further confirm that the observed increase does not depend from a higher concentration of cells (in fact, the negative control contains the same amount of cells as the positive control).

The presence of inhibition zones at the edges of the plate was also taken into account as an important indication of antibacterial activity on *H. pylori* for each strain "as such", i.e. irrespective of the possible effect of co-administered antibiotic agents and/or possible generic immunostimulating effects on the organism. This activity was further confirmed in "agar well diffusion" experiments. Even a bactericidal activity was observed in vitro, performing a "time kill curve": La-14 and Bl-04 caused a decrease of *H. pylori* viable count of 3 logarithms (from 10^8 cfu/ml to 10^5 cfu/ml) in 3 hours, and a total killing of *H. pylori* in 72 hours. It is here important to note that a mere immunostimulating activity (occasionally reported in the literature for some probiotics) is generally insufficient to eradicate infections, especially in case of *H. pylori*; in fact, this bacterium causes a weak activation of the immune response being itself responsible for part of the pathogenicity of this infection. By contrast, the presence of a direct inhibitory activity of the present strains on *H. pylori* makes them useful not as mere adjuvants, but as primary therapeutic agents directed against *H. pylori* infection. Also when used in a combined treatment with antibiotics, the present probiotics are not qualifiable as mere adjuvating immunostimulants, as they exert a direct antibacterial activity which potentiates that of the co-administered antibiotic agent, thus providing the basis for a potent combined treatment.

5. Adjuvant Effect of Probiotic Supernatant on Antibiotic Activity

To investigate on a possible adjuvant or favourable effect of *L. acidophilus* La-14 and *B. animalis lactis* Bl-04 towards the anti-*helicobacter* activity of amoxicillin and clarithromycin, the Checkerboard method was used on a 96-well plate. 200 µl of probiotic supernatant cultivated in MRS broth were poured into the first well of the first row (H1, starting concentration, 1:2) and 200 µl of the antibiotic in the other wells of the first column (H2-H12); 100 µl of *Brucella* broth—containing 10% inactivated fetal calf serum, were added to the remaining wells. After all substances were two-fold diluted in a horizontal sense, 100 µl of the probiotics supernatant was added to each well of the third row containing different concentrations of the antibiotic (H3-A3); afterwards, the dilution of the extract was carried out in a vertical sense. A12 well was the negative control (without any substance, FIG. 2). In this way, each different well from the third raw downward contained the two substances at different concentration. Bacteria from 48-hour plate cultures were suspended in *Brucella* broth at 10¨8 organisms per ml. Two microlitres of bacteria suspension were dropped onto each of 96 wells containing the various concentrations of the substances under examination. Microplates were incubated in a microaerobic environment at 37° C. for 24 h. MICs were determined as for the broth dilution (first not turbid well). Three µl of mixtures were then sub-cultured from each well onto Petri dishes containing *Pylori agar*; dishes were incubated in a microaerobic environment at 37° C. for 3 days. MBC was regarded as the lowest concentration of antibiotic whose subculture on *agar* showed the complete absence of bacterial growth. Results were the average of two determinations. All tests were performed in duplicate and were repeated three times.

The obtained results are as follows:

Clarithromycin MIC towards the *H. pylori* strain was 12 µg/ml (MBC: 24 µg/ml). MIC of amoxicillin was 0.25 µg/ml (MBC: 0.5 µg/ml). When probiotic supernatant was added to antibiotics, we observed a strong reduction of both MIC and MBC values:

Clarithromycin MIC became 0.125 µg/ml, almost 1/100 of the original MIC (in the same way, MBC became 0.25 µg/ml)

Amoxicillin MIC became 0.00025 µg/ml, 1/1000 of the original MIC (in the same way, MBC became 0.0005 µg/ml).

Therefore the antibiotic activity against *H. pylori* increased by 100 folds (clarithromycin) and 1000 folds (amoxicillin).

The above data refer to *L. acidophilus* La-14; equivalent results were found for *B. lactis* Bl-04.

In summary, the present *L. acidophilus* and *B. lactis* strains proved to increase the antimicrobial activity of against *H. pylori* in a huge way. In addition, they exhibited a strong antibacterial synergy vs. *H. pylori* when tested together in vitro. DNA sequencing demonstrates the total absence of plasmids. The number of nucleotidic mutations of both the chemoresistant species configures them as new variants, completely different from the original clones.

REFERENCES

Hooi J K Y, Lai W Y, Ng W K, Suen M M Y, Underwood F E, Tanyingoh D, Malfertheiner P, Graham D Y, Wong V W S, Wu J C Y, Chan F K L, Sung J J Y, Kaplan G G, Ng S C. Global Prevalence of *Helicobacter pylori* infection: systematic review and meta-analysis. Gastroenterology. 2017 Aug.; 153(2):420-429. doi: 10.1053/j.gastro.2017.04.022. Epub 2017 Apr. 27. Review. PubMed PMID: 28456631.

Suerbaum S, Michetti P. *Helicobacter pylori* infection. N Engl J Med. 2002; 347(15):1175-86. Review. PubMed PMID: 12374879.

Alba C, Blanco A, Alarcon T. Antibiotic resistance in *Helicobacter pylori*. Curr Opin Infect Dis. 2017 Oct.; 30(5):489-497. doi: 10.1097/QC0.0000000000000396. Review. PubMed PMID: 28704226.

Dang Y, Reinhardt J D, Zhou X, Zhang G. The effect of probiotics supplementation on *Helicobacter pylori* eradication rates and side effects during eradication therapy: a meta-analysis. PLoS One. 2014 Nov. 3; 9(11):e111030. doi:10.1371/journal.pone.0111030. eCollection 2014. PubMed PMID: 25365320; PubMed Central PMCID: PMC4217763.

Malfertheiner P, Meqraud F, O'Morain C A, Atherton J, Axon A T, et al. (2012) Management of *Helicobacter pylori* infection—the Masstricht IV/Florence Consensus Report. Gut 61: 646-64.

Borriello S P, Hammes W P, Holzapfel W, Marteau P, Schrezenmeir J, Vaara M, Valtonen V. Safety of probiotics that contain lactobacilli or bifidobacteria. Clin Infect Dis. 2003 Mar. 15; 36(6):775-80. Epub 2003 Mar. 5. Review. PubMed PMID: 12627362.

Foligne B, Nutten S, Grangette C, Dennin V, Goudercourt D, Poiret S, Dewulf J, Brassart D, Mercenier A, Pot B. Correlation between in vitro and in vivo immunomodulatory properties of lactic acid bacteria. World J Gastroenterol. 2007 Jan. 14; 13(2):236-43. PubMed PMID: 17226902; PubMed Central PMCID: PMC4065951.

Štšepetova J, Taelma H, Smidt I, Hütt P, Lapp E, Aotaht E, Mandar R. Assessment of phenotypic and genotypic antibiotic susceptibility of vaginal *Lactobacillus* sp. J Appl Microbiol. 2017 August; 123(2):524-534. doi: 10.1111/jam.13497. PubMed PMID: 28574626.

Morovic W, Roper J M, Smith A B, Mukerji P, Stahl B, Rae J C, Ouwehand A C. Safety evaluation of HOWARU(®) Restore (*Lactobacillus acidophilus* NCFM, *Lactobacillus paracasei* Lpc-37, *Bifidobacterium animalis* subsp. *lactis* Bl-04 and *B. lactis* Bi-07) for antibiotic resistance, genomic risk factors, and acute toxicity. Food Chem Toxicol. 2017 Dec.; 110:316-324. doi: 10.1016/j.fct.2017.10.037. Epub 2017 Nov. 5. PubMed PMID: 29080807.

Figura N, Marcolongo R, Cavallo G, Santucci A, Collodel G, Spreafico A, Moretti E. Polysorbate 80 and *Helicobacter pylori*: a microbiological and ultrastructural study. BMC Microbiol. 2012 Sep. 22; 12:217. doi: 10.1186/1471-2180-12-217. PubMed PMID: 22998649; PubMed Central PMCID:PMC3537525.

Cekin A., Sahinturk Y, Harmandar F A, Uyar S., Yocular B O, Cekin Y. Use of probiotics as an adjuvant to sequential *H. pylori* eradication therapy: Impact on eradication rates, treatment resistance, treatment-related side effects and patient compliance. Turk J. Gastroenterol., 2017, 28, pp. 3-11.

Dang y, Reinhardt J D, Zhou X, Zhang G, The effect of probiotics supplementation on *Helicobacter pylori* eradication rates and side effects during eradication therapy: a meta-analysis. PLOS ONE, www.plosone.org, Nov. 2014, 9(11), pp. 1-15.

Collado M C, Gonzales A, Gonzales R, Hernandez M, Ferrus M A, Sanz Y. Antimicrobial peptides are among the antagonistic metabolites produced by *Bifidobacterium* against Helicobacer *pylori*. International Journal of Antimicrobial Agents, 2005, 25, pp. 385-391.

Mcfarland L V, Huang Y, Wang L, Malfertheiner P. Systematic review and meta-analysis: multi-strain probiotics as adjunct therapy for *Helicobacter pylori* eradication and prevention of adverse effects. United European Gastroenterology Journal, 2016, 4(4), pp. 546-561.

The invention claimed is:

1. A probiotic microorganism selected from the group consisting of:
   *Lactobacillus acidophilus* La-14 clone LAA8 (deposit number: DPS RE RSCIC 5);
   *Lactobacillus acidophilus* La-14 clone LAC6 (deposit number: DPS RE RSCIC 6);
   *Bifidobacterium animalis lactis* Bl-04 clone BLAC86 (deposit number: DPS RE RSCIC 7);
   *Bifidobacterium animalis lactis* Bl-04 clone BLA8 (deposit number: DPS RE RSCIC 8); and
   *Bifidobacterium animalis lactis* Bl-04 clone BLC6 (deposit number: DPS RE RSCIC 9),
   and combinations thereof.

2. The probiotic microorganism or microorganisms according to claim 1, combined as follows:
   one or more among *Lactobacillus acidophilus* La-14 clone LAA8 (deposit number: DPS RE RSCIC 5); and *Lactobacillus acidophilus* La-14 clone LACE (deposit number: DPS RE RSCIC 6);
   and one or more among *Bifidobacterium animalis* lacks Bl-04 clone BLAC86 (deposit number: DPS RE RSCIC 7); *Bifidobacterium animalis lactis* Bl-04 clone BLAB (deposit number: DPS RE RSCIC 8);
   and 13*Bifidobacterium animalis lactis* Bl-04 clone BLC6 (deposit number: DPS RE RSCIC 9).

3. A method of treating *Helicobacter pylori* infections in a patient in need thereof, comprising administering to said patient one or more probiotic microorganisms of claim 1.

4. The method according to claim 3, in association with administration of an antibiotic treatment directed against *Helicobacter pylori* infections.

5. The method according to claim 4, wherein said antibiotic is amoxicillin and/or clarithromycin.

6. The method according to claim 4, wherein the antibiotic is administered jointly with the probiotic, microorganism or microorganisms, or separately therefore.

7. A composition comprising one or more probiotic microorganism or microorganisms, of claim 1, in association with pharmaceutically acceptable excipients and/or ingredients.

8. The composition according to claim 7, further comprising one or more antibiotics directed against *Helicobacter pylori* infections.

9. The composition according to claim 8 further comprising amoxicillin and/or clarithromycin.

10. The composition according to claim 7, in a form suitable for oral administration.

11. The composition according to claim 10, in a form selected from the group consisting of: tablets, capsules, microcapsules, pills, lozenges, dragees, adhesive films, powders, granulates, solutions, suspensions, emulsions, microemulsions, liposomes, gels, syrups, elixirs, chewing gum, drops, sprays, and aerosols.

12. A kit comprising the probiotic of claim 1, and an antibiotic directed against *Helicobacter pylori*.

13. The kit according to claim 12 in the form of a blister comprising one or more dosage forms containing the probiotic microorganism or microorganisms of claim 1, and one or more dosage forms containing the antibiotic against *Helicobacter pylori*.

* * * * *

SEQUENCE LISTING

<160> NUMBER OF SEQ ID NOS: 1

<210> SEQ ID NO 1
<211> LENGTH: 13
<212> TYPE: DNA
<213> ORGANISM: Lactobacillus acidophilus

<400> SEQUENCE: 1
gtcacgtagt tgt